United States Patent
Wieczorek et al.

(10) Patent No.: US 6,252,927 B1
(45) Date of Patent: Jun. 26, 2001

(54) METHOD OF MANUFACTURING A SCINTILLATOR AND A SCINTILLATOR LAYER THUS MANUFACTURED

(75) Inventors: Herfried K. Wieczorek; Stefan Schneider, both of Aachen; Josef Lauter, Geilenkirchen, all of (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/428,775

(22) Filed: Oct. 28, 1999

(30) Foreign Application Priority Data

Oct. 28, 1998 (EP) .................................................. 98203651
Dec. 30, 1998 (EP) .................................................. 98204494

(51) Int. Cl.⁷ ........................................................ G01T 1/20
(52) U.S. Cl. ...................... 378/19; 250/367; 250/370.09; 250/370.11
(58) Field of Search ........................ 378/19; 250/370.09, 250/370.11, 368, 367

(56) References Cited

U.S. PATENT DOCUMENTS

| | | | |
|---|---|---|---|
| 4,725,734 | * 2/1988 | Nishiki | 378/19 |
| 4,940,901 | 7/1990 | Henry et al. | 250/370.09 |
| 4,945,243 | 7/1990 | Arques | 250/367 |
| 5,378,894 | * 1/1995 | Akai | 250/367 |

FOREIGN PATENT DOCUMENTS

| | | |
|---|---|---|
| 0440282A2 | 8/1991 | (EP) . |
| 0486102A1 | 5/1992 | (EP) . |
| 0588397A2 | 3/1994 | (EP) . |
| 0911836 | 4/1999 | (EP) . |
| WO9504289 | 2/1995 | (WO) . |

* cited by examiner

Primary Examiner—Robert H. Kim
Assistant Examiner—Drew A. Dunn
(74) Attorney, Agent, or Firm—John F. Vodopia

(57) ABSTRACT

In order to manufacture a scintillator layer for a detector for the detection of electromagnetic radiation, transmitted by an object, which has a high spatial resolution and only a slight interaction between the scintillator elements, it is proposed to pour a molten mass of a radiation-absorbing metal, having a melting point below 350° C., into intermediate spaces which extend vertically between neighboring scintillator elements.

13 Claims, 1 Drawing Sheet

METHOD OF MANUFACTURING A SCINTILLATOR AND A SCINTILLATOR LAYER THUS MANUFACTURED

BACKGROUND OF THE INVENTION

1. Field of the Invention

The invention relates to a method of manufacturing a scintillator layer for a detector for the detection of electromagnetic radiation transmitted by an object, in which a scintillator layer for converting the radiation of a first energy level into radiation of a second energy level is provided on a photosensor layer for converting such radiation into an electric current, and in which the scintillator layer, comprising a plurality of scintillator elements, is provided with intermediate layers which extend in the vertical direction along the side faces of the scintillator elements.

2. Description of Related Art

Scintillator layers of detectors which are used, for example in computer tomographs, customarily consist of cadmium tungstate [CWO] ($CdWO_4$), of yttrium gadolinium oxide [YGO] ($(Y,Gd)_2O_3$:E) or of gadolinium oxysulphides [GOS] ($Gd_2O_2S$:Pr). Such materials provide conversion of radiation of a first energy level into radiation of a second energy level, for example, the conversion of X-rays into visible light in the case of computer tomographs.

The international patent application WO 95/04289 describes a detector with a scintillator layer which consists of a two-dimensional array of scintillator elements, i.e. a plurality of rows of scintillator elements arranged parallel to one another. The scintillator elements are formed by monocrystals. Between the scintillator elements there are provided optical separation layers which extend along the side faces of the scintillator elements. These layers are provided with a thickness of from 0.05 to 1 $\mu$m by metal deposition. The materials used for these layers are aluminium, tungsten, molybdenum, iron, chromium, nickel, gold, silver or copper.

Since recently it is attempted to enhance the resolution, and hence the image quality, of X-ray examination devices, notably computer tomographs, by utilizing detectors comprising a larger number of detector elements or scintillator elements. This gain in respect of optical resolution, however, is accompanied by the drawback of increased crosstalk between neighboring scintillator elements, which increase is due to the crossing over of photons and X-ray quanta.

Citation of a reference herein, or throughout this specification, is not to construed as an admission that such reference is prior art to the Applicant's invention of the invention subsequently claimed.

SUMMARY OF THE INVENTION

It is an object of the present invention to propose a method of manufacturing a scintillator layer for a detector which has a higher resolution and in which the disturbing interaction between the scintillator elements is only insignificant.

This object is achieved by means of the method which is characterized as described in the claims as well as by means of the scintillator layer which is characterized as described in the claims.

The basic idea of the invention is to pour in a molten mass of a radiation-absorbing metal, having a melting point below 350° C., into the intermediate spaces between neighboring scintillator elements.

The molten mass may consist of pure radiation-absorbing metals, preferably lead, bismuth and mercury which have melting points of 327.5, 271.3 and 33.4° C., respectively. Molten masses of lead and bismuth solidify at room temperature. Mercury is liquid at room temperature. The metal is retained by layers which enclose the scintillator layer as a whole.

Preferably, use is made of metal alloys whose components can be selected from the following group of metals: bismuth and/or lead and/or zinc and/or tin and/or cadmium and/or mercury. Preferably, compositions of the components which correspond to the eutectic compounds are selected.

The described choice of metals and metal alloys offers a particularly attractive low melting point in combination with a high absorptivity. The pouring method enables the formation of thin intermediate layers which do not unnecessarily reduce the active surface area of the scintillator element. Because of the choice of metals having melting points below 350° C., chemical reactions with the scintillator crystals or damage are avoided.

The radiation-absorbing layers have two functions. First of all, they serve as an optical separation layer in that they reflect photons arising during the conversion (optical crosstalk) back to the individual scintillator elements, so that they increase the signal strength. The intermediate layers extend in the vertical direction, i.e. transversely to or perpendicularly to the surface of the scintillator layer.

On the other hand, such layers serve for the absorption of K fluorescence X-ray quanta (X-ray crosstalk). K fluorescence X-ray quanta or secondary X-ray quanta arise when the energy of the electromagnetic radiation or X-rays is not fully taken up by the scintillator elements. In the case of the described scintillator metals GOS and CWO such K fluorescence X-ray quanta amount to from 40 to 50% of the primary absorbed radiation. This is because the energy of the absorbed X-ray quanta exceeds the so-al led K-edge energy of the scintillator crystal. Only a part of the K fluorescence X-ray quanta then arising can be absorbed in the same scintillator element; a further part is emitted and a third part is absorbed by neighboring crystals. The proposed poured absorption layers prevent such X-ray crosstalk between neighboring scintillator elements.

Known layers of materials such as molybdenum offer only an unsatisfactory optical separation function of this kind in conjunction with a high absorptivity for secondary X-rays. The same also holds for known optical separation layers of titanium dioxide embedded in epoxy resin. Therefore, such materials can be used only for one-dimensional detectors with a low spatial resolution; such one-dimensional detectors involve less crosstalk of X-ray quanta in comparison with two-dimensional detectors.

The proposed pouring method enables optimum filling of the gaps between the scintillator elements. Fillings with a width of preferably 100 $\mu$m can be realized in a fast, easily reproducible and inexpensive manner. The method is, therefore, very suitable for the manufacture of scintillators composed of a large number of scintillator elements in a flat arrangement.

The pouring process is preferably performed in vacuum or in an inert gas atmosphere. This has a positive effect on the fluidity of the molten metal.

The preparation of gaps along the side faces of the scintillator elements, and hence of a pattern of recesses to be filled with molten metal, is realized on the one hand by arranging monocrystals in such a manner that a minimum distance is maintained. On the other hand, a pattern of recesses can be mechanically formed in a scintillator layer, for example by sawing by means of an appropriate tool. This method enables the formation of a large number of individual scintillator elements. After the filling of the gaps or the pattern of recesses with the molten metal, a remaining non-filled edge zone of the scintillator layer can be mechanically removed.

The proposed method of manufacturing a scintillator layer for a detector is particularly suitable for a two-dimensional scintillator layer, i.e. an array of scintillator elements with n rows and m columns, where n, m are numbers larger than 1. The method, however, is also suitable for the manufacture of the scintillator layer of one-dimensional or linear detectors.

Assuming a two-dimensional detector or a cone beam detector provided with a scintillator array, a version of the method according to the invention is proposed in which the radiation-absorbing layers are poured into the gaps between the rows of scintillator elements whereas the radiation-absorbing layers are inserted as preformed thin layers or foils in the gaps between the columns of scintillator elements. The reverse situation is also feasible. The preformed metal layers are preferably made of lead, tantalum, tungsten or gadolinium. Whereas the insertion of preformed metal layers into the gaps of a linear scintillator for a one-dimensional detector would still be feasible in practice, such a method would be faced with excessive mechanical problems and problems in respect of time in the case of two-dimensional detectors. The dressing of linear segments and their flat arrangement is feasible, but involves technical problems because of the low hardness of the metals and the associated resilience of the layers during cutting.

Some examples of preferred radiation-absorbing metal alloys and their melting points will be given hereinafter.
1) An alloy consisting of 56.5% by weight of bismuth, 43.5% by weight of lead (binary eutectic).
   Melting point: 125° C.; density: 10.42 g/cm3.
2) An Alloy consisting of 55.0% by weight of bismuth, 43.0% by weight of lead, 2.0% by weight of zinc (ternary eutectic).
   Melting point: 124° C.; density: 10.32 g/cm3.
3) An alloy consisting of 52.5% by weight of bismuth, 32.0% by weight of lead, 15.5% by weight of tin (ternary eutectic).
   Melting point: 96° C.; density: 9.69 g/cm3.
4) An alloy consisting of 51.7% by weight of bismuth, 40.2% by weight of lead, 8.1% by weight of cadmium (ternary eutectic).
   Melting point: 91.5° C.; density: 10.24 g/cm3.
5) An alloy consisting of 49.5% by weight of bismuth, 27.3% by weight of lead, 13.1% by weight of tin, 10.1% by weight of cadmium (quaternary eutectic, Lipowitz's metal).
   Melting point: 71° C.; density: 9.57 g/cm3.
6) An alloy consisting of 50.0% by weight of bismuth, 25.0% by weight of lead, 12.5% by weight of tin, 12.5% by weight of cadmium (Wood's metal).
   Melting point: 70° C.

BRIEF DESCRIPTION OF THE DRAWINGS

Further details and advantages of the invention are apparent from and will be elucidated, by way of non-limitative example, with reference to the embodiment which is shown in the Figures.

DETAILED DESCRIPTION OF THE PREFERRED EMBODIMENT

Figure 1:
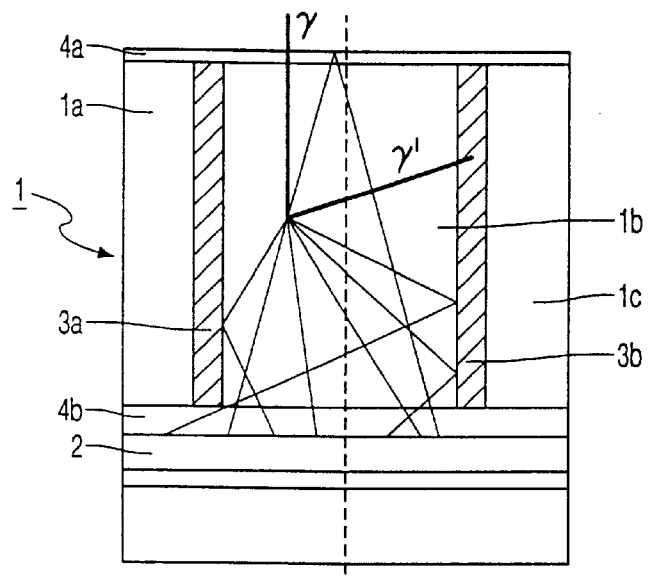
FIG. 1 is a cross-sectional view of a detector provided with a scintillator layer formed by means of the proposed method.

The detector consists of a scintillator layer 1 and a photodiode array 2 which is situated therebelow. The photodiode array 2 is connected to amplifiers and, via the amplifiers, to multiplexers (diagrammatically represented by subsequent layers). The signals of the multiplexers are applied to an arithmetic unit via an analog-to-digital converter.

The scintillator layer 1 itself consists of a plurality of scintillator elements (in this case 1a, 1b, 1c). Intermediate layers 3a, 3b of radiation-absorbing metals, having a melting point below 350° C., are poured into a pattern of recesses along the side faces of the scintillator elements. The scintillator layer is completely enclosed by a reflection or protection layer (4a, 4b).

When the detector is exposed to X-rays, the X-ray quanta (y) in the individual scintillator elements (in this case shown in 1b by way of example) are converted into photons. The intermediate layers 3a, 3b then serve as optical separation layers in that they reflect the photons back to the individual elements. Any K fluorescent X-ray quanta (y') occurring are absorbed by the intermediate layers 3a, 3b so that undesirable X-ray crosstalk is avoided.

The scintillator layers manufactured in conformity with the method according to the invention are suitable for use in all known detectors. Also included are, for example so-called flat solid-state X-ray detectors with large electronic circuits. Detectors of this kind may also be referred to as X-ray sensor matrices and are known, for example from European patent application 0 440 282 A2. The detectors provided with the proposed scintillator layer are used notably in computer tomographs.

Figure 2:
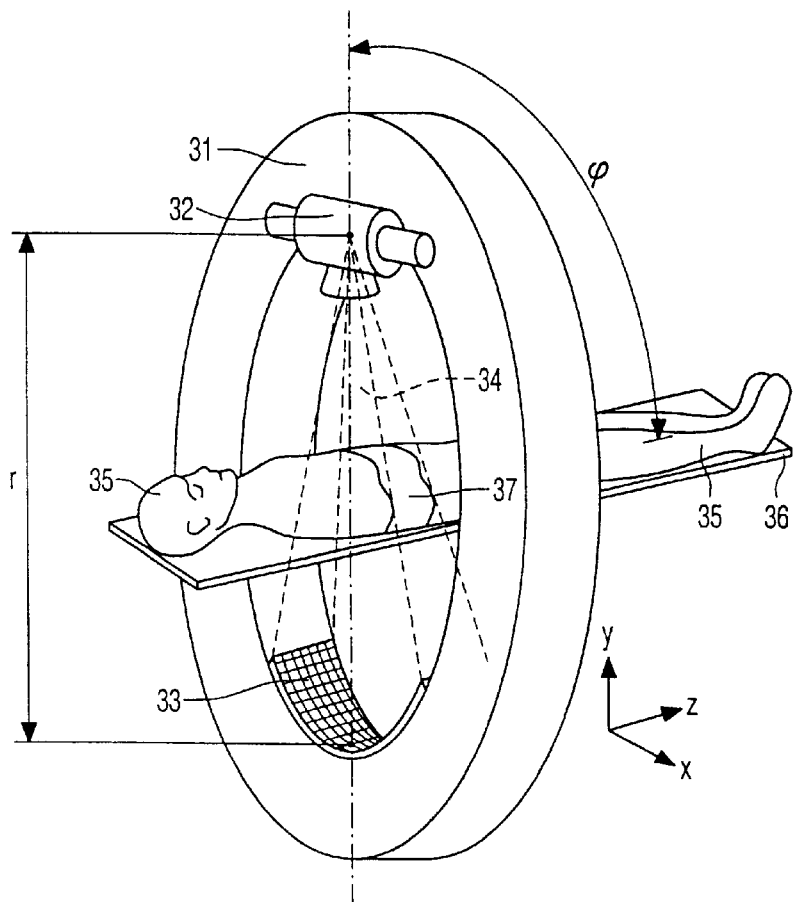
FIG. 2 is a diagrammatic view of a computer tomograph provided with multi-line detector.

FIG. 2 shows diagrammatically a computer tomograph provided with a multi-line detector. In a circular portal frame or gantry 31 there are arranged the X-ray source 32 and the multi-line detector 33 which is mounted so as to face the tube. The X-ray tube 32 projects a pyramidal X-ray beam 34 through the patient 35 and onto the multi-line detector 33. For the purpose of examination the patient 35 is displaced through the rotating gantry 31 on a table 36.

The detector array 33 is arranged at a distance r from the focus of the X-ray tube 32. During a complete revolution of the gantry 31 the X-ray beam 34 irradiates the patient 35 within the plane of the gantry from different angles φ relative to the perpendicular. A cross-sectional image 37 of the irradiated region of the patient is calculated by means of these projections.

The detector array 33 is composed of a plurality of detector elements which are arranged in a plurality of rows. These rows extend parallel to one another in the direction of the axis of rotation (z direction). The detector array includes the photodiode array 2.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method of manufacturing a scintillator layer for a detector for the detection of electromagnetic radiation transmitted by an object, in which a scintillator layer for converting the radiation of a first energy level into radiation of a second energy level is provided on a photosensor layer for converting such radiation into an electric current, and in which the scintillator layer, comprising a plurality of scintillator elements, is provided with intermediate layers which extend in the vertical direction along the side faces of the scintillator elements, comprising providing the intermediate layers by pouring a molten mass of a radiation-absorbing metal having a melting point below 350° C.

2. A method as claimed in claim 1 wherein the metal is lead or bismuth or mercury.

3. A method as claimed in claim 1 wherein the metal is an alloy composed of the constituents bismuth and/or lead and/or zinc and/or tin and/or cadmium and/or mercury.

4. A method as claimed in claim 3 wherein the compositions of the metal alloys are chosen to be such that they correspond to the eutectic of the compounds.

5. A method as claimed in claim 1 wherein the pouring process takes place in vacuum or in an inert gas atmosphere.

6. A method as claimed in claim 1 further comprising preparing the intermediate spaces along the side faces of the scintillator elements by arranging the scintillator elements at a distance from one another as monocrystals.

7. A method as claimed in claim 1 further comprising preparing the intermediate spaces along the side faces of the scintillator elements by mechanically forming a pattern of recesses in a flat scintillator layer.

8. A method as claimed in claim 1, wherein the scintillator layer comprises an array of scintillator elements with n rows and m columns, where n, m are numbers larger than 1.

9. A method as claimed in claim 8 wherein the step of providing further comprises pouring a liquefied metal into the intermediate spaces of the rows of scintillator elements, and inserting preformed metal layers into the intermediate spaces of the columns of scintillator elements, or vice versa.

10. A scintillator layer for a detector for the detection of electromagnetic radiation transmitted by an object in order to convert radiation of a first energy level into radiation of a second energy level, the scintillator layer comprising a plurality of scintillator elements deposited over a photosensor layer for converting radiation of the second energy level into an electric current, and intermediate layers vertically extending along the side faces of the scintillator elements wherein the intermediate layers are formed by a poured radiation-absorbing metal having a melting point below 350° C.

11. A detector comprising a scintillator layer as claimed in claim 10.

12. A detector as claimed in claim 11, wherein the detector is a flat solid-state X-ray detector.

13. A computer tomograph comprising:

an X-ray source for emitting an X-ray beam, the X-ray beam being rotatable about a system axis, a detector as claimed in claim 11 on which the X-ray beam is incident, and an arithmetic unit for calculating images of the examined object on the basis of the detector signals formed for the various projections.

* * * * *